(12) United States Patent
Simhadri et al.

(10) Patent No.: US 9,382,207 B2
(45) Date of Patent: Jul. 5, 2016

(54) PROCESS FOR THE PREPARATION OF ATAZANAVIR BISULFATE

(71) Applicant: Laurus Labs Private Limited, Hyderabad (IN)

(72) Inventors: Srinivas Simhadri, Hyderabad (IN); Yaseen Mohammad, Hyderabad (IN); Venkata Sunil Kumar Indukuri, Hyderabad (IN); Seeta Ramanjaneyulu Gorantla, Hyderabad (IN)

(73) Assignee: Laurus Labs Private Limited, Hyderabad (IN)

( * ) Notice: Subject to any disclaimer, the term of this patent is extended or adjusted under 35 U.S.C. 154(b) by 0 days.

(21) Appl. No.: 14/423,464

(22) PCT Filed: Aug. 22, 2013

(86) PCT No.: PCT/IN2013/000508
§ 371 (c)(1),
(2) Date: Feb. 24, 2015

(87) PCT Pub. No.: WO2014/030173
PCT Pub. Date: Feb. 27, 2014

(65) Prior Publication Data
US 2015/0183742 A1 Jul. 2, 2015

(30) Foreign Application Priority Data
Aug. 24, 2012 (IN) ............ 3487/CHE/2012

(51) Int. Cl.
*C07D 213/56* (2006.01)
*C07D 213/42* (2006.01)

(52) U.S. Cl.
CPC ............ *C07D 213/56* (2013.01); *C07D 213/42* (2013.01)

(58) Field of Classification Search
None
See application file for complete search history.

(56) References Cited

U.S. PATENT DOCUMENTS

| 5,849,911 | A | 12/1998 | Fassler et al. |
| 6,087,383 | A | 7/2000 | Singh et al. |
| 7,829,720 | B2 | 11/2010 | Kim et al. |
| 8,461,347 | B2 | 6/2013 | Kao et al. |

OTHER PUBLICATIONS

Zhongmin, et al.; "Process Research and Development for an Efficient Synthesis of the HIV Protease Inhibitor BMS-232632"; The Bristol-Myers Squibb Pharmaceutical Research Institute; Organic Process Research & Development 2002, vol. 6, No. 3, 323-328; 6 pages.

Xing, et al.; "An Efficient and Practical Synthesis of the HIV Protease Inhibitor Atazanavir via a Highly Diastereoselective Reduction Approach"; State Key Laboratory of Drug Research, Shanghai Institute of Materia Medica, Shanghai Institutes for Biological Sciences; Organic Process Research & Development 2008, vol. 12, No. 1, 69-75; 7 pages.

*Primary Examiner* — Zinna Northington Davis
(74) *Attorney, Agent, or Firm* — Blank Rome LLP; Brian W. Higgins; Francine F. Li

(57) ABSTRACT

The present invention relates to an improved process for the preparation of Atazanavir bisulfate Form A. The present invention also relates to a pharmaceutical composition using the Atazanavir bisulfate Form A of the invention.

16 Claims, 1 Drawing Sheet

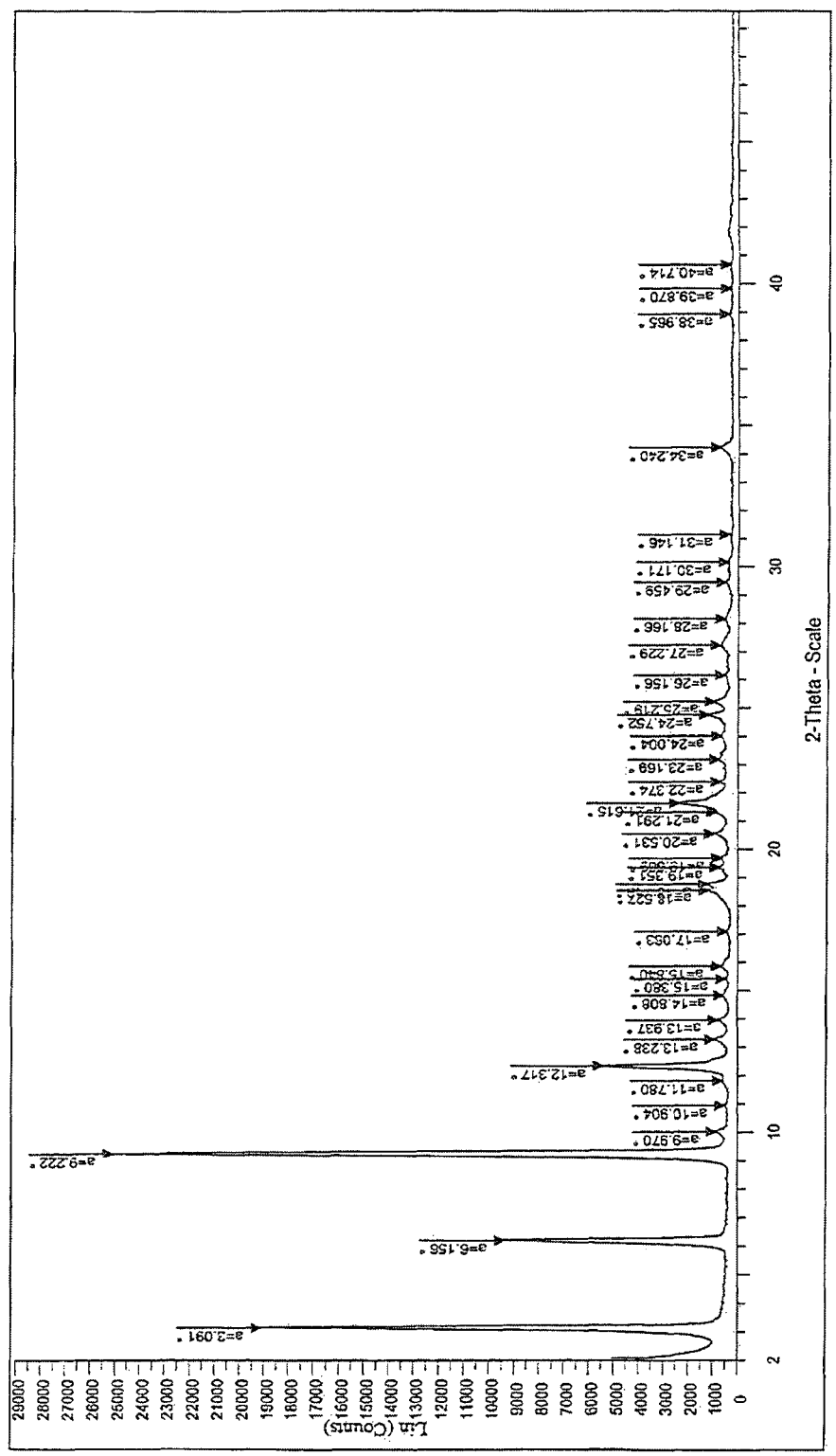

PROCESS FOR THE PREPARATION OF ATAZANAVIR BISULFATE

CROSS REFERENCE TO RELATED APPLICATIONS

This application claims the benefit under Indian Provisional Application No. 3487/CHE/2012, filed on Aug. 24, 2012 entitled "An improved process for the preparation of atazanavir bisulfate", the contents of which is incorporated by reference herein.

FIELD OF THE INVENTION

The present invention relates to an improved process for the preparation of Atazanavir and its pharmaceutically acceptable salts thereof, particularly Atazanavir bisulfate in polymorphic Form A.

BACKGROUND OF THE INVENTION

Atazanavir bisulfate, also known as (3S,8S,9S,12S)-3,12-bis(1,1-dimethylethyl)-8-hydroxy-4,11-dioxo-9-(phenylmethyl)-6-[[4-(2-pyridinyl)phenyl]methyl]-2,5,6,10,13-pentaaza-tetradecane dioic acid dimethyl ester, sulfate (1:1), and it is represented by the following structure:

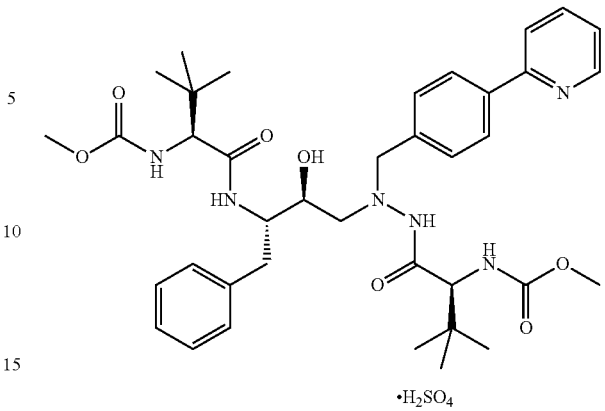

Atazanavir bisulfate is marketed under the brand name of REYATAZ and is indicated in combination with other anti-retroviral agents for the treatment of HIV-1 infection. REYATAZ capsules are available for oral administration in strengths containing the equivalent of 100 mg, 150 mg, 200 mg, or 300 mg of atazanavir as atazanavir sulfate.

U.S. Pat. No. 5,849,911 ("the '911 patent") discloses a series of azapeptide HIV protease inhibitors such as Atazanavir. The '911 patent further discloses a process for the preparation of azapeptide HIV protease inhibitor Atazanavir by coupling the epoxide with a hydrazine carbamate in the presence of isopropyl alcohol to form the protected diamine, the protected diamine is treated with HCl to form diamine, the diamine is isolated and coupled with N-methoxycarbonyl-L-tert-leucine to obtain Atazanavir free base.

The process disclosed in the '911 patent is schematically represented as follows:

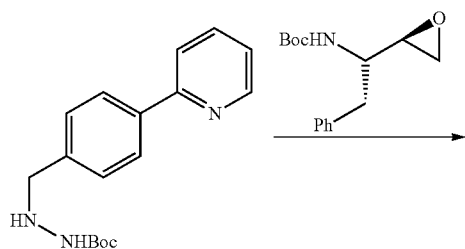

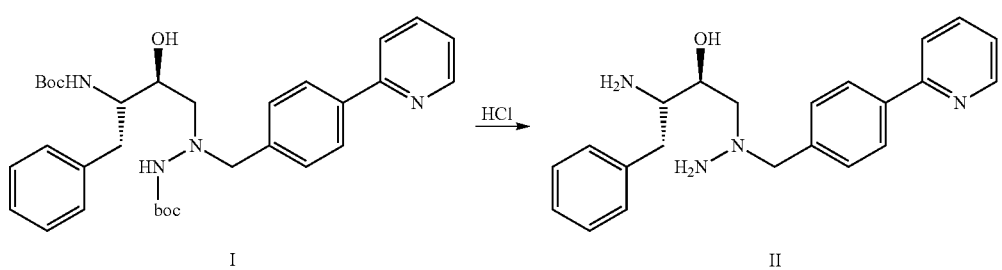

-continued

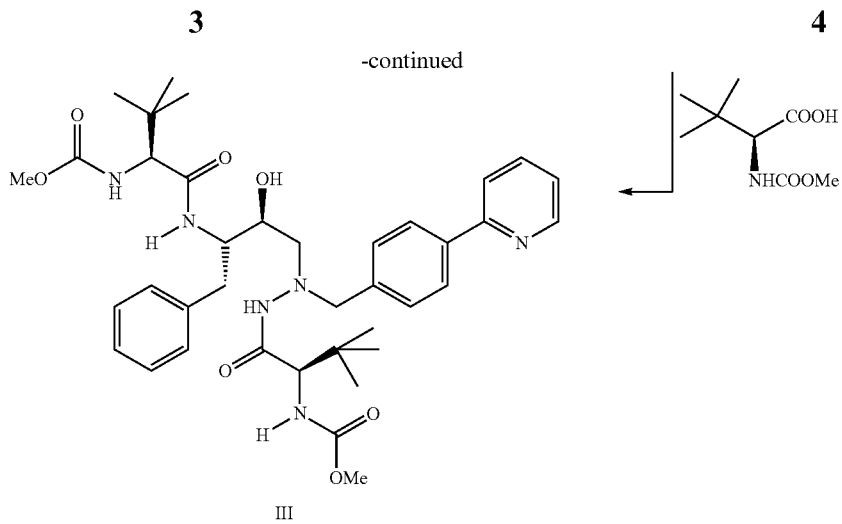

III

In the '911 patent, atazanavir methane sulfonate is precipitated with ether from methylene chloride solution thereof followed by drying under reduced pressure; whereas atazanavir hydrochloride is precipitated by mixing dioxane solution of atazanavir with dioxane solution of hydrochloride. However this patent remains silent about the sulfate salt preparation.

U.S. Pat. No. 6,087,383 ("the '383 patent") discloses atazanavir bisulfate and process for the preparation of the same in two crystalline polymorphs such as Type-I and Type-II crystals. The '383 patent further discloses that the Type-I crystals are anhydrous/desolvated crystals whereas the Type-II crystals are hydrated, hygroscopic crystals. The Type-I crystals are prepared by adding sulfuric acid in to a suspension of atazanavir free base and a solvent such as acetonitrile, ethanol-heptane or acetone followed by seeding the crystals. The Type-II crystals are prepared by adding sulfuric acid in to a suspension of atazanavir free base and isopropanol chilled in an ice-bath, stirring the suspension at room temperature and seeding Type-I crystals.

Organic Process Research and Development, 6, p. 323-328 (2002) describes the preparation of Type-I crystals of atazanavir sulfate by adding sulfuric acid in to a solution of atazanavir free base in ethanol and then adding n-heptane and seed crystals.

Organic Process Research and Development, 12, p. 69-75 (2008) discloses crystallization of atazanavir free base with ethanol-water solvent system.

U.S. Pat. No. 7,829,720 ("the '720 patent") discloses an improved process for the preparation of Atazanavir bisulfate Form A crystals (which are referred to as Type-I crystals in US '383 patent) by a modified cubic crystallization technique in which sulfuric acid is added at an increasing rate according to a cubic equation, a relatively larger, more well defined atazanavir bisulfate crystals, along with a narrower particle size range and fewer fines are provided, than a constant addition rate crystallization. The '720 patent described that the crystal particle size and morphology of the atazanavir bisulfate salt are dependent on the addition rate of the sulfuric acid, which determines the crystallization rate.

The '720 patent process includes the steps of reacting a solution of atazanavir free base in an organic solvent (in which the atazanavir bisulfate salt is substantially insoluble) with a first portion of sulfuric acid in an amount to react with less than about 15%, by weight of the atazanavir free base, adding seeds of atazanavir bisulfate Form A crystals to the reaction mixture, adding additional sulfuric acid in multiple stages accurately at increasing rates according to a cubic equation to effect formation of Form A crystals.

U.S. Pat. No. 8,461,347 ("the '347 patent") discloses an improved process for the preparation of Atazanavir bisulfate Form A crystals by solvent and antisolvent method.

The processes for preparation of Atazanavir bisulfate described in the above literature have certain drawbacks as it involves either formation of undesired crystals by standard addition of sulfuric acid or formation of desired Form A crystals by incorporating special limitations such as calculated quantity of acid addition at different increasing intervals at a specific time intervals and at a specific temperature in order to achieve controlled crystallization, which are not viable and burdensome for those of ordinary skill in the art, particularly in commercial scale operations.

Hence, there remains a need in the art for an improved process to prepare pharmaceutically desirable Atazanavir bisulfate Form A crystals, which is feasible at large scale, in terms of ease and cost-effective. The inventors found an improved process for preparing atazanavir Form A crystals under controlled crystallization conditions, where the improvements include additional sulfuric acid is added in a continuous manner without involving aforementioned limitations.

SUMMARY OF THE INVENTION

The present invention encompasses an improved process for the preparation of Atazanavir and its pharmaceutically acceptable salts thereof, particularly Atazanavir bisulfate in polymorphic Form A.

In accordance with one embodiment, the present invention provides an improved process for preparation of crystalline Atazanavir bisulfate Form A, comprising:
a) providing a solution of Atazanavir free base in one or more organic solvents,
b) adding first portion of sulfuric acid of about 15% to about 25% by weight of the total sulfuric acid,
c) optionally seeding the reaction solution with Atazanavir bisulfate Form A seed crystals,
d) adding second portion of sulfuric acid in a continuous manner, and
e) isolating the crystalline Atazanavir bisulfate Form A.

In accordance with a second embodiment, the present invention provides an improved process for preparation of crystalline Atazanavir bisulfate Form A, comprising:

a) providing a solution of Atazanavir free base in one or more organic solvents, wherein the one or more organic solvent being selected from the group consisting of ketones, halogenated solvents, dipolar aprotic solvents or mixtures thereof, b) adding first portion of sulfuric acid of about 15% to about 25% by weight of the total sulfuric acid at room temperature, c) optionally seeding the reaction mass with Atazanavir bisulfate Form A seed crystals, d) heating the reaction solution to about 35° C. to about 75° C., e) adding second portion of sulfuric acid in a continuous manner at a temperature of about 35° C. to about 75° C., f) cooling the solution to about 10° C. to about 30° C., and g) isolating the crystalline Atazanavir bisulfate Form A.

In accordance with a third embodiment, the one or more organic solvent is selected from the group consisting of acetone, methylene chloride, dimethyl formamide, N-methyl pyrrolidone, dimethyl sulfoxide or mixtures thereof.

In accordance with a fourth embodiment, the one or more organic solvent is mixture of acetone and dimethyl formamide.

In accordance with a fifth embodiment, the one or more organic solvent is mixture of acetone and dimethyl sulfoxide.

In accordance with a sixth embodiment, the present invention provides a one pot process for preparation of crystalline Atazanavir bisulfate Form A, comprising:

a) reacting 1-[4-(pyridine-2-yl)phenyl]-5(S)-2,5-bis[(tert-butyloxycarbonyl)amino]-4(S)-hydroxy-6-phenyl-2-azahexane of formula I with an acid to obtain 1-[4-(pyridin-2-yl)-phenyl]-4(S)-hydroxy-5(S)-2,5-diamino-6-phenyl-2-azahexane trihydrochloride of formula II as trihydrochloride salt,

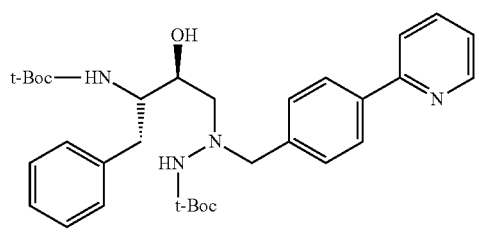

I

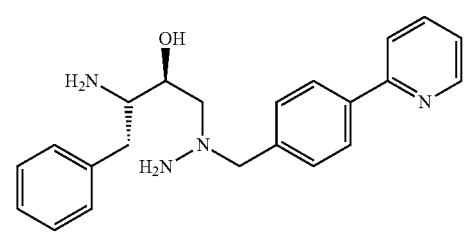

II b) in-situly reacting the resultant compound of formula II with N-methoxycarbonyl-L-tert-leucine active ester to obtain atazanavir free base, c) dissolving the atazanavir crude obtained from step (b) in one or more organic solvents, wherein the one or more organic solvents being selected from the group consisting of ketones, halogenated solvents, dipolar aprotic solvents or mixtures thereof, d) adding first portion of sulfuric acid of about 15% to about 25% by weight of the total sulfuric acid, e) optionally seeding the reaction mass with Atazanavir bisulfate Form A seed crystals, f) adding second portion of sulfuric acid in a continuous manner, and g) isolating the crystalline Atazanavir bisulfate Form A.

In accordance with a seventh embodiment, the present invention provides pharmaceutical composition comprising crystalline Atazanavir bisulfate Form A prepared by the processes of the present invention and at least one pharmaceutically acceptable excipient.

BRIEF DESCRIPTION OF THE DRAWINGS

The accompanying drawing, which is incorporated in and constitute a part of this specification, illustrate several embodiments of the invention and together with the description, serve to explain the principles of the invention.

FIG. 1 is the characteristic powder X-ray diffraction (XRD) pattern of Atazanavir sulfate Form A.

DETAILED DESCRIPTION OF THE INVENTION

The present invention provides an improved process for the preparation of crystalline Atazanavir bisulfate Form A. The invention provides a large scale process of crystalline Atazanavir bisulfate Form A using industrially feasible processes and selective conditions to crystallize substantially pure Form A crystals such as selection of solvent medium and mode of isolation techniques including the temperatures.

In one embodiment, the present invention provides an improved process for preparation of crystalline Atazanavir bisulfate Form A, comprising:

a) providing a solution of Atazanavir free base in one or more organic solvents, b) adding first portion of sulfuric acid of about 15% to about 25% by weight of the total sulfuric acid, c) optionally seeding the reaction solution with Atazanavir bisulfate Form A seed crystals, d) adding second portion of sulfuric acid in a continuous manner, and e) isolating the crystalline Atazanavir bisulfate Form A.

The atazanavir free base in the solution may be any crystalline or other forms of atazanavir free base or atazanavir obtaining an existing solution from a previous processing step.

The step of providing a solution of atazanavir free base may be include dissolving any form of atazanavir free base in one or more organic solvents. The one or more organic solvent includes but is not limited to ketones, halogenated solvents, dipolar aprotic solvents or mixtures thereof.

Preferably, the one or more organic solvent is selected from the group consisting of acetone, methylene chloride, dimethyl formamide, N-methyl pyrrolidone, dimethyl sulfoxide or mixtures thereof; more preferably the solvent is a mixture of acetone and dimethyl formamide or a mixture of acetone and dimethyl sulfoxide.

The first portion of sulfuric acid may be about 15% to about 25% by weight of the total sulfuric acid, preferably about 20% and sulfuric acid may be about 95 to about 100% sulfuric acid.

The first portion of sulfuric acid may be added at a temperature of about 10° C. to about 65° C., preferably at about 20° C. to about 45° C., more preferably at about 25° C. to about 35° C.

The first portion of sulfuric acid may be added by addition in one lot or over a period of about 10 minutes to about 60 minutes, preferably about 30 minute.

Then, the solution may be heated to about 35° C. to about 75° C., preferably about 45° C. to 50° C. and then, the reaction is seeded with atazanavir bisulfate Form A crystals and allowed stirred for a period from about 10 minutes to about 60 minutes, preferably from about 30 minutes.

The quantity of seed crystals may be from about 0.1% to about 50% of the atazanavir free base, preferably from about 1% to about 10%.

Then, the reaction solution may be continue stirring at temperature of about 35° C. to about 75° C., preferably about 45° C. to 50° C., at this time the solution may be transformed to slight hazy reaction solution.

Step d) of foregoing process, the second portion of sulfuric acid may be added in a continuous addition manner without any predefined increasing rate at a temperature of about 35° C. to about 75° C., preferably about 45° C. to 50° C. to precipitating atazanavir bisulfate crystals.

The second portion of sulfuric acid may be added continuously over a period of about 2 hours to about 10 hours, preferably about 3 hours to about 7 hours, more preferably about 5 hours.

Thereafter, the resultant solution may be allowed to continue stirring until crystallization completes. Preferably the stirring may be continued over a period from about 30 minutes to about 4 hours, more preferably about 60 minutes.

Step e) of isolating the crystalline atazanavir bisulfate Form A may be carried out by cooling the resultant reaction solution at a temperature from about 30° C. or less, preferably about 20° C. to 25° C. such that the atazanavir bisulfate Form A can be isolated by conventional techniques, for example filtration. In the event that stirring is involved, the temperature during stirring can range from about 20° C. to 25° C. for a period from about 30 minutes to about 5 hours, preferably about 3 hours.

The resultant product may optionally be further dried. Drying can be suitably carried out in a tray dryer, vacuum oven, air oven, fluidized bed drier, spin flash dryer, flash dryer and the like. The drying can be carried out at a temperature ranging from about 30° C. to about 75° C., preferably from about 40° C. to about 55° C.

The present invention advantageously provides crystalline Atazanavir bisulfate Form A, obtained by the process described herein, having a chemical purity of at least about 98%, as measured by HPLC, preferably at least about 99%, as measured by HPLC, and more preferably at least about 99.8%, as measured by HPLC.

The present invention provides an advantageous process for preparing Atazanavir bisulfate Form A. For instance, the process of the instant invention described herein, circumvents the use of unmanageable process limitations for example, cubic crystallization method by multiple addition of sulfuric acid at increasing rates as described in the '720 patent. In contrast, the process herein described the use of normal addition of sulfuric acid in a continuous manner. Moreover, the present invention described herein, advantageously and consistently reproduces the Atazanavir bisulfate Form A crystals with a pharmaceutically acceptable purity.

Further, the reported literature for preparation of Atazanavir bisulfate Form A, for example US '383 patent involves Atazanavir free base is treated with continuous addition of sulfuric acid followed by seeding the pure Form A crystals, resulting uncontrolled crystallization. In contrast, the process herein described results a controlled crystallization to produce Form A crystals by using a predetermined quantity of sulfuric acid for the first portion and continuous manner of addition of second portion of sulfuric acid.

In another embodiment, the present invention provides an improved process for preparation of crystalline Atazanavir bisulfate Form A, comprising:

a) reacting 1-[4-(pyridine-2-yl)phenyl]-5(S)-2,5-bis[(tert-butyloxycarbonyl)amino]-4(5)-hydroxy-6-phenyl-2-azahexane of formula I with an acid to obtain 1-[4-(pyridin-2-yl)-phenyl]-4(S)-hydroxy-5(S)-2,5-diamino-6-phenyl-2-azahexane trihydrochloride of formula II as trihydrochloride salt,

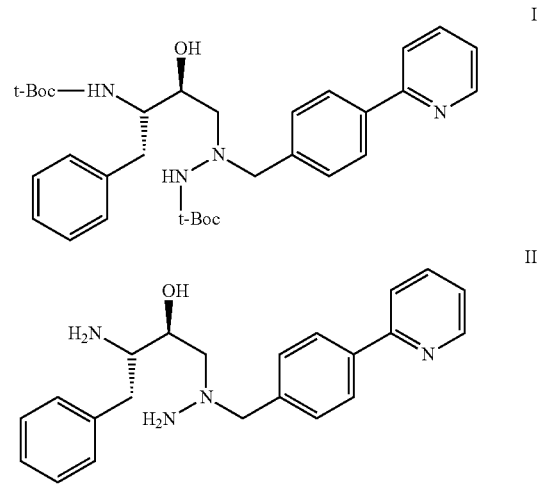

b) in-situly reacting the resultant compound of formula II with N-methoxycarbonyl-L-tert-leucine active ester to obtain atazanavir free base, c) dissolving the atazanavir base crude obtained from step (b) in one or more organic solvents, wherein the one or more organic solvents being selected from the group consisting of ketones, halogenated solvents, dipolar aprotic solvents or mixtures thereof, d) adding first portion of sulfuric acid of about 15% to about 25% by weight of the total sulfuric acid, e) optionally seeding the reaction mass with Atazanavir bisulfate Form A seed crystals, f) adding second portion of sulfuric acid in a continuous manner, and g) isolating the crystalline Atazanavir bisulfate Form A.

The compound of Formula I is known in the art and can be produced by methods known and recognized by the organic chemist of ordinary skill in the art. For example, such a process is described in U.S. Pat. No. 5,849,911 which is included by reference herein in its entirety.

Step (a) of the foregoing process includes the deprotection of the two t-Boc protecting groups with an acid, preferably hydrochloric acid in the presence of an organic solvent at ambient temperature to reflux. The organic solvent includes, but is not limited to halogenated solvents such as methylene chloride, ethylene chloride, chloroform and the like; alcohols such as methanol, ethanol, isopropanol and the like; ethers such as tetrahydrofuran and the like; preferably methylene chloride.

After completion of the deprotection reaction, the resultant reaction mass may be extracted with water and then the resulting aqueous layer containing triamine compound of Formula II can be further processed directly without isolating as an intermediate stage.

The resultant triamine compound of Formula II may be reacted with N-methoxycarbonyl-L-tert-leucine active ester in the presence of a base in an organic solvent at a temperature within the range from about 25 to about 50° C. to obtain atazanavir free base. The base include, but is not limited to dipotassium hydrogen phosphate, diisopropylethylamine, N-methylmorpholine, sodium carbonate, or potassium carbonate; preferably dipotassium hydrogen phosphate and the organic solvent include, but is not limited to methylene chloride, a mixture of ethyl acetate and butyl acetate, acetonitrile or ethyl acetate, preferably methylene chloride.

The atazanavir free base obtained from the process described above can processed directly without isolating as solid material.

The present invention provides crystalline atazanavir bisulfate Form A, obtained by a process comprising providing atazanavir free base as obtained by the process described above, as a starting material or as an intermediate, where the resultant atazanavir bisulfate substantially in atazanavir bisulfate Form A crystals.

In an embodiment, the present invention provides an improved process for preparation of crystalline Atazanavir bisulfate Form A, comprising atazanavir free base as obtained by the process described as just above is converted in to atazanavir bisulfate Form A crystals by a process of the present invention.

EXAMPLES

The following non limiting examples illustrate specific embodiments of the present invention. They are not intended to be limiting the scope of the present invention in any way.

Example 1

Preparation of Atazanavir Free Base

Part A: A 2.0 L round bottom flask fitted with a mechanical stirrer, thermometer socket was charged with methylene chloride (500 ml) and 1-[4-(pyridine-2-yl)phenyl]-5(S)-2,5-bis[(tert-butyloxycarbonyl)amino]-4(S)-hydroxy-6-phenyl-2-azahexane (100 g) at 25-30° C. The reaction mass was allowed to cool to 0-5° C. and CP HCl (78 ml) was added over a period of 30 minutes at same temperature. The reaction mass was heated to reflux temperature and stirred for about 1 hour at 35-40° C. The reaction mixture was allowed to cool to 25-30° C. and extracted the product with water (160 ml+50 ml). The separated aqueous layer processed for next step.

Part B: A 3.0 L round bottom flask fitted with a mechanical stirrer, thermometer socket was charged with methylene chloride (900 ml) and N-methylxycarbonyl-L-tert-leucine (84 g). The reaction mass was allowed to cool to 20-30° C. and anhydrous hydroxy benzotriazole (HOBT) (64.8 g) and 1-(3-dimethylaminopropyl)-3-ethylcarbodiimide hydrochloride (EDC.HCl) (92.0 g) was charged. The reaction mass was stirred for 2 hr at 20-30° C. and dipotassium hydrogen phosphate solution was added (249 g of dipotassium hydrogen phosphate in 1130 ml water) and then Part-A triamine trihydrochloride solution at same temperature. The reaction mass was heated to about 35-40° C. and stirred for 4 hours. The reaction mass was allowed to cool to 25-30° C. and the organic layer was separated. The organic layer was washed with sodium phosphate monobasic dihydrate solution (880 ml) then 2% sodium hydroxide solution (800 ml) followed by 10% sodium chloride solution (475 ml). The separated organic layer containing atazanavir free base processed for next step.

Example 2

Preparation of Atazanavir Bisulfate Form A

To the free base solution in a 3.0 L, 3-neck round-bottom flask was added DMSO (60 ml) at 25-30° C. The solution was concentrated to about 350 ml of the reaction mass. The solution was allowed to cool to 25-30° C. and acetone (500 ml) was added then the mixture was concentrated to about 400 ml. To the concentrate free base solution, acetone (1400 ml) was added. The solution was stirred for 15 minutes at 25-30° C. and 3.83 g of first portion of sulfuric acid was added over a period of 30 minutes. The reaction solution was heated to 45-50° C. and atazanavir bisulfate (5.0 g) Form A seeding material was charged. The reaction mass was stirred for 30 minutes at 45-50° C. and 15.34 g of second portion of sulfuric acid was added over a period of 5 hours by using addition funnel at 45-50° C. The mass was stirred for 60 minutes at 45-50° C. and then allowed to cool to 20-25° C. and stirred for 3 hours at same temperature. Precipitated solid was filtered and washed with acetone. The wet product was dried at about 50° C. to about 55° C. under reduced pressure to provide the title compound. Yield: 123 gms. HPLC purity: 99.9%.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

What is claimed is:

1. A process for preparing crystalline Atazanavir bisulfate Form A, comprising the steps of:
    a) providing a solution of Atazanavir free base in one or more organic solvents,
    b) adding a first amount of sulfuric acid to the solution, wherein the first amount is about 15% to about 25% by weight of a pre-determined amount of sulfuric acid used in total,
    c) optionally seeding the reaction solution with Atazanavir bisulfate Form A seed crystals,
    d) adding the remaining pre-determined amount of sulfuric acid, wherein the remaining amount is added at a controlled crystalline-forming continuous rate, and
    e) isolating the crystalline Atazanavir bisulfate Form A.

2. The process of claim 1, wherein the one or more organic solvents are selected from the group consisting of a ketone, a halogenated solvent, a dipolar aprotic solvent, and a mixture thereof.

3. The process of claim 2, wherein the one or more organic solvents are selected from the group consisting of acetone, methylene chloride, dimethyl formamide, N-methyl pyrrolidone, dimethyl sulfoxide, and a mixture thereof.

4. The process of claim 3, wherein the one or more organic solvents are a mixture of acetone and dimethyl formamide.

5. The process of claim 3, wherein the one or more organic solvents are a mixture of acetone and dimethyl sulfoxide.

6. The process of claim 1, wherein the first amount of sulfuric acid is about 20% by weight of the pre-determined amount of sulfuric acid used in total.

7. The process of claim 1, wherein the first amount of sulfuric acid is added at a temperature of about 10° C. to about 65° C.

8. The process of claim 7, wherein the first amount of sulfuric acid is added at a temperature of about 25° C. to about 35° C.

9. The process of claim 1, wherein the first amount of sulfuric acid is added over a period of about 30 minutes.

10. The process of claim 1, wherein the seed crystals is about 1% to about 10% of the atazanavir free base in quantity.

11. The process of claim 10, wherein the seed crystals is about 5% of the atazanavir free base in quantity.

12. The process of claim 1, wherein the remaining amount of sulfuric acid is continuously added at a temperature of about 35° C. to about 70° C.

13. The process of claim 12, wherein the remaining amount of sulfuric acid is continuously added at a temperature of about 45° C. to about 50° C.

14. The process of claim 1, wherein the remaining amount of sulfuric acid is continuously added over a period of about 3 hours to about 7 hours.

15. The process of claim 14, wherein the remaining amount of sulfuric acid is continuously added over a period of about 5 hours.

16. A process for preparing crystalline Atazanavir bisulfate Form A, comprising the steps of:
   a) providing a solution of Atazanavir free base in one or more organic solvents;
   b) adding a first amount of sulfuric acid to the solution to form a mixture, wherein the first amount is about 20% by weight of a pre-determined amount of sulfuric acid used in total, and is added at a temperature of about 25° C. to about 35° C. over a period of about 30 minutes;
   c) seeding the reaction solution with Atazanavir bisulfate Form A seed crystals over a period of about 30 minutes;
   d) adding the remaining pre-determined amount of sulfuric acid, wherein the remaining amount is added at a controlled crystalline-forming continuous rate, and is added at a temperature of about 45° C. to about 50° C. over a period of about 5 hours; and
   e) isolating the crystalline Atazanavir bisulfate Form A.

* * * * *